United States Patent [19]

Kosaka

[11] 4,345,458
[45] Aug. 24, 1982

[54] WATER TANK ASSEMBLY FOR A PRESSURE RESISTANCE MEASURING APPARATUS FOR TESTING CONTAINERS

[75] Inventor: Jiro Kosaka, Zama, Japan

[73] Assignee: Meiko Industry Corporation, Limited, Nihonbashi, Japan

[21] Appl. No.: 201,988

[22] Filed: Oct. 29, 1980

[30] Foreign Application Priority Data

Jul. 19, 1980 [JP] Japan ............................ 55-102256[U]

[51] Int. Cl.³ ............................................ G01B 13/24
[52] U.S. Cl. ...................................... 73/37.5; 73/45.5
[58] Field of Search ...................... 73/37.5, 37.8, 45.5, 73/41.2, 41.3, 41.4

[56] References Cited

U.S. PATENT DOCUMENTS

| | | | |
|---|---|---|---|
| 2,055,568 | 9/1936 | Wilsdorf | 73/45.5 |
| 2,697,935 | 12/1954 | Gordon | 73/45.5 |
| 3,768,305 | 10/1973 | Pechko et al. | 73/45.5 |
| 4,089,208 | 5/1978 | Franks et al. | 73/45.5 |

*Primary Examiner*—Donald O. Woodiel
*Attorney, Agent, or Firm*—Oblon, Fisher, Spivak, McClelland & Maier

[57] ABSTRACT

A water tank assembly for a pressure resistance measuring apparatus for testing containers comprises a vertical water tank, an auxiliary water tank connected with the vertical water tank at an upper end portion of the vertical tank wherein the vertical tank has a smaller diameter than that of the auxiliary water tank, a cover attached to the vertical water tank, a nozzle assembly connected to the cover wherein a container to be tested is fixed to the lower end of the nozzle assembly, an opening end portion of the vertical water tank protruding into the auxiliary water tank, and wherein the vertical water tank and the auxiliary water tank store water and the water level of the auxiliary water tank is above the upper end portion of the vertical water tank.

2 Claims, 3 Drawing Figures

WATER TANK ASSEMBLY FOR A PRESSURE RESISTANCE MEASURING APPARATUS FOR TESTING CONTAINERS

BACKGROUND OF THE INVENTION

1. Field of the Invention

This invention relates to the structure of a water tank for a pressure resistance measuring apparatus for testing containers.

2. Description of the Prior Art

Generally, containers, such as liquefied propane gas containers and oxygen containers, are under a legal obligation to be subjected to pressure resistance measurement in their manufacture and to then be reinspected. The purpose of the pressure resistance measurement test is to certify the pressure resistant property and to examine the sufficiency of elasticity of the containers. Containers without leakage, abnormal linear expansion and a permanent increment ratio under a prescribed standard are then allowed to be used.

Conventionally, the water tank method or the non-water tank method has been used in the pressure resistance measurement test. The water tank apparatus used for the water tank method includes a water supply pipe for supplying tap water (low-pressure water) to a water tank and a water pipe connecting a buret with the water tank. A cover supporting a container is fixed to the water tank filled with water to support the container in the water, water is supplied into the water tank to deaerate the water tank and then the zero point of the buret is set, thus completing the test preparation.

In the test, the container is pressurized to a prescribed test pressure and kept at that pressure for a fixed period of time to examine the pressure drop and measure the expansion of the container by the total increment of the water in the buret. The permanent linear expansion of the container is measured by the permanent increment of the water in the buret after reducing the pressure in the container to normal pressure. The permanent increment ratio of the container is determined using the measured permanent increment and the total increment.

In measurements, using the conventional apparatus, an excessive amount of time for preparation of the measurement is required in replacing the tested container with the next container to be tested, supplying tap water to fill up the water tank through the water supply pipe and deaerating the water tank after a series of measurements, which reduces the efficiency of the measurement.

SUMMARY OF THE INVENTION

Accordingly, an object of the present invention is to provide a water tank assembly for a pressure resistance measuring apparatus for testing containers capable of improving the efficiency of the measuring operation.

According to the present invention, the structure includes an auxiliary water tank united with a vertical water tank at the upper end of the vertical tank having a smaller diameter than that of the auxiliary water tank, a cover provided with a nozzle assembly and attached to the vertical water tank with a container to be tested fixed to the lower end of the nozzle assembly, the opening end of the vertical water tank protruding into the auxiliary water tank, the vertical water tank and the auxiliary tank storing water and the water level of the auxiliary water tank being above the upper end of the vertical water tank.

The upper end of the vertical water tank may be aligned with the bottom face of the auxiliary water tank protruded into the auxiliary water tank formed with a reduced diameter relative to the diameter of the body providing the same diameter for the vertical water tank and the auxiliary water tank so that the vertical water tank and the auxiliary water tank are united in the forms of -shape, -shape or -shape, respectively.

Another object of the present invention is to substantially reduce leakage of the high pressure air into the water jacket due to the disposition of junctions between the first nozzle and the second nozzle and the second nozzle and the containers to be tested in the water jacket and to secure normal measurement by eliminating unnecessary disposition of junctions in the water jacket except the junction of the second nozzle and the container to be tested, which is unavoidable.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein.

DETAILED DESCRIPTION OF THE PREFERRED EMBODIMENT

Figure 1:
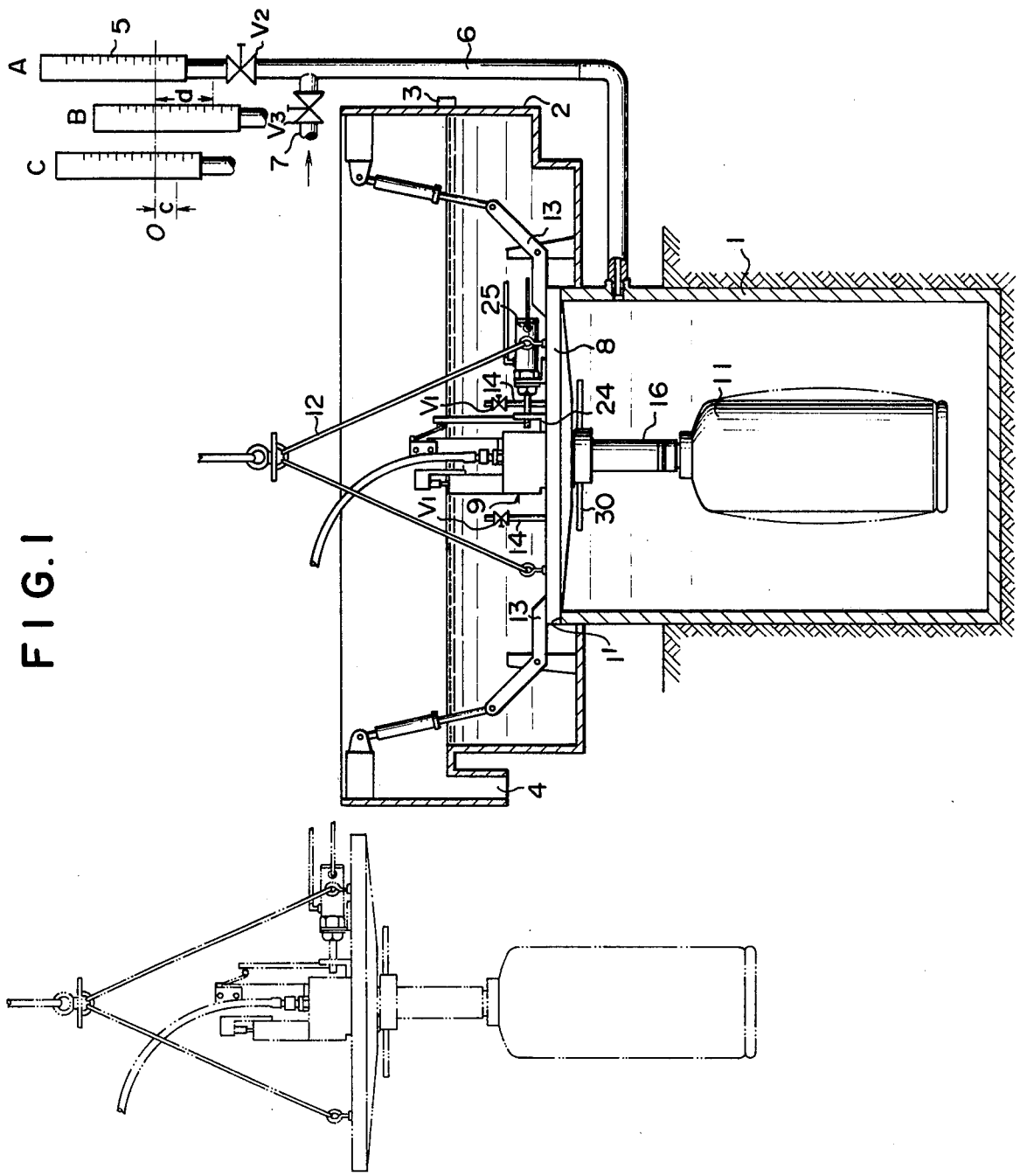
FIG. 1 is an elevational view, partly in section, of the water tank apparatus of the present invention.
Figure 2:
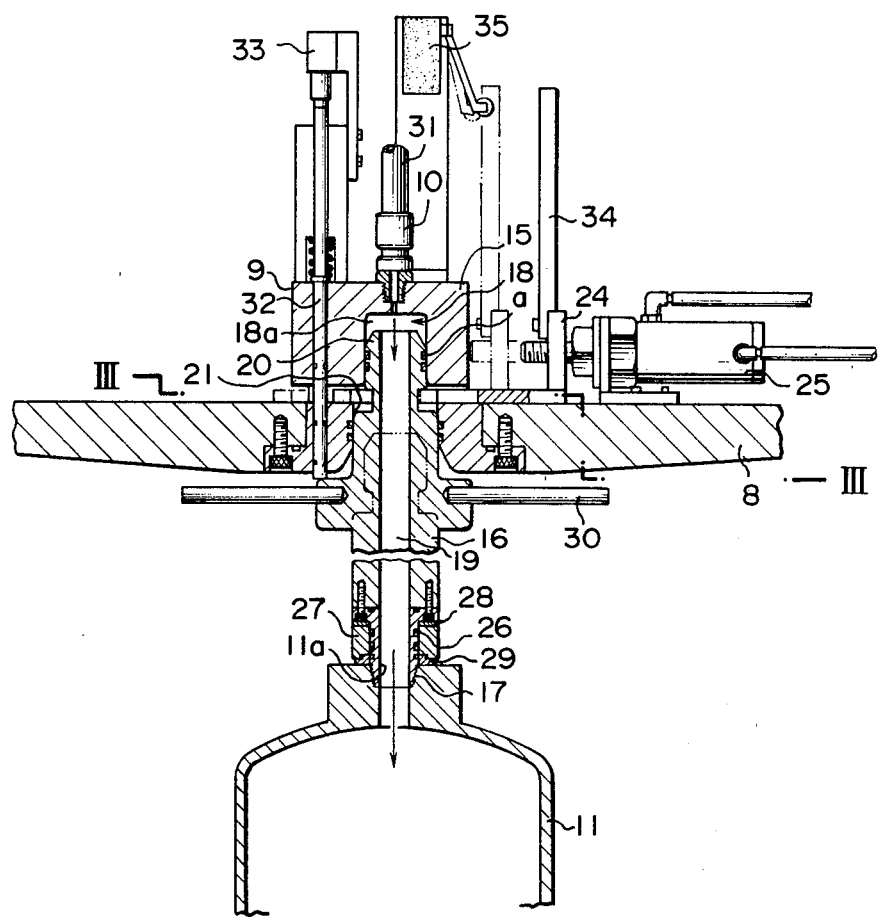
FIG. 2 is an enlarged elevational view, partly in section of the nozzle section.
Figure 3:
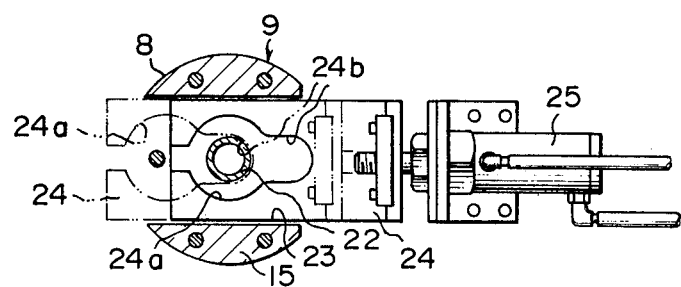
FIG. 3 is a cross-sectional view taken on line III—III of FIG. 2.

Explanation will be made hereinafter of a preferred embodiment of the present invention referring to the attached drawings. A principal water tank 1 is a bottomed circular or square barrel. The principal water tank 1 is installed with most of it buried under the floor and the upper part presented above the floor.

An auxiliary water tank 2 is mounted on the upper part of the principal water tank 1 at the bottom wall of the auxiliary water tank 2 with the upper end 1' of the principal water tank 1 protruding into the auxiliary water tank 2.

The auxiliary water tank 2 is a circular- or square-shaped vessel having a larger bottom relative to the upper end of the principal water tank 1. Tap water is continuously supplied into the auxiliary water tank 2 through a low-pressure water inlet 3 provided on the side wall of auxiliary water tank 2 and connected to a tap or a water reservoir. An overflow outlet 4 is provided on the side wall of the auxiliary water tank above the upper end 1' of the principal water tank 1.

Tap water supplied through the low pressure water inlet 3 flows through the upper end 1' into the principal water tank 1 and, after filling up the principal water tank 1, is stored in the auxiliary water tank 2. The water level of the auxiliary water tank 2 is maintained at a fixed level corresponding to the height of the overflow outlet 4.

A tube 6 connects a buret 5 to the upper part of the principal water tank 1. A water inlet 7 for zero point setting of the buret 5 is provided for the tube 6. The water inlet 7 is connected to a tap or a reservoir. A cover 8 is detachably fixed to the upper end 1' of the principal water tank 1.

A nozzle assembly 9 is fixed at the center of the cover 8 so as to penetrate through the cover 8. The nozzle assembly 9 is provided with a high pressure inlet 10 connected to a hydraulic pump. The cover 8 can be turned or vertically moved relative to the principal water tank 1 with a wire 12 of a container carrier (not shown). In preparing for measurement, the cap 8 is dismounted from the principal water tank 1, a container 11 to be tested is attached to the nozzle 9, the container 11 is filled with water, the cap 8 is mounted on the principal water tank 1 from above the principal water tank 1 thus immersing the container 11 in the water contained in the principal water tank 1, and is then fixed to the upper end 1' in the water contained in the auxiliary water tank 2. Clamp mechanisms 13 provided for the auxiliary water tank 2 press and fix the periphery of the cover 8 to the brim of the upper end 1' of the principal water tank 1.

A projecting vent 14 is provided for the cover 8. Stop valves ($V_1$), ($V_2$) and ($V_3$) are provided for the vent 14, the tube 6 and the water supply pipe 7, respectively.

Nozzle assembly 9 consists of a first nozzle 15 disposed above cover 8 and second nozzle 16 detachably joined with the first nozzle 15 and disposed below cover 8. The lower end of first nozzle 15 is fixed to the upper face of cover 8 which is lifted with wire 13. Container 11 for containing propane gas or the like is screwed onto the second nozzle 16 by engaging mouth 11a with threaded lower end 17 of second nozzle 2. First and second nozzles 15 and 16 are tubular members having axial fluid passages 18 and 19, respectively. The lower half of fluid passage 18 of first nozzle 15 is enlarged to form a joining part 18a. Second nozzle 16 penetrates cover 8 from a position beneath cover 8 upward through hole 21 fromed on cover 8 and is movable relative to the cover. Joint 20 of second nozzle 16 is inserted into joining part 18a of first nozzle 15, thus joining first and second nozzles 15 and 16 at a joining position (a) above cover 8. Grooved neck 22 is formed under joint 20 of second nozzle 16. Guide groove 23 is formed at joining part 18a of first nozzle 15 facing through hole 23 of cover 8. Clamping plate 24 is slidable along guide groove 23.

Clamping plate 24 is moved along guide groove 23 manually, or, as illustrated, mechanically by power cylinder 25. Circular hole 24a of a diameter smaller than that of joint 20 and slightly larger than the diameter of neck 22 are formed on clamping plate 24. Clamping plate 24 detachably supports second nozzle 16 with slot 24b. Rotary member 27 is rotatably restrained on the reduced lower end of second nozzle with an O-ring 26 also being positioned on the reduced lower end.

Spacer 28 made of a self-lubricating material of a suitable hardness, such as acrylic resin, is put between rotary member 27 and the shoulder of second nozzle 16. Annular sealing member 29 is positioned under rotary member 27 for sealing mouth 11a of container 11. Operating handle 30 is used for turning second nozzle 16.

The pressure resistance measuring procedure will be explained hereinafter regarding the apparatus as described above. First, second nozzle 16 is separated from first nozzle 15 and screwed into mouth 11a of container 11. Second nozzle 16 and container 11 are securely joined together by turning second nozzle 16 with the operating handle 30. Secondly, first nozzle 15 descends together with cover 8 over second nozzle 16 with a lifting mechanism (not shown) thus closely fitting joint 20 of second nozzle 16 in the joining part 18a of the first nozzle through the through hole 21 and circular hole 24a of clamping plate 24. First nozzle 15 and second nozzle 16 are securely connected with the clamp by the engagement of slot 24b with neck 22 of second nozzle 15.

Then, the assembly of cover 8, nozzle assembly 9 and container 11 is carried and lowered over the principal water tank 1 with a lifting mechanism (not shown) and nozzle assembly 9 and container 11 are immersed in the water contained in principal water tank 1 and cover 8 is fastened to the upper end 1' of principal water tank 1. Finally, high pressure water is introduced into container 11 through a hose 31 and nozzle assembly 9 to pressurize container 11 for the pressure resistance measurement. More specifically, cover 8 carrying container 11 is fixed to the upper end 1' of the principal water tank 1 with the stop valve ($V_1$) opened and the stop valves ($V_2$) and ($V_3$) closed while water is continuously supplied into the auxiliary water tank through water inlet 3 to immerse container 11 in the water, then the stop valve ($V_1$) is closed and the stop valves ($V_2$) and ($V_3$) are opened thus connecting buret 5 to the principal water tank 1 with tube 6 to set the zero point of buret 5 as illustrated by state (A).

After closing stop valve ($V_3$), high pressure water is introduced into container 11 through a high pressure water inlet 10 and nozzle assembly 9 to raise the interior pressure of container 11 up to the prescribed test pressure. Container 11 is left pressurized for a fixed period of time (30 sec.) to substantially expand the container.

Container 11 expands and the volume of the container increases due to the pressurization causing a resultant increment of the water in buret 5. The total increment (d) is measured by setting the upper surface of the water in the buret to the zero point by lowering buret 5 (state B).

After the measurement of the total increment, the pressure in container 11 is released from pressurization and the interior pressure reduces to zero so that the volume of container 11 is restored to near the original volume. The restored volume is slightly larger than the original volume due to the residual strain of container 11 caused by the pressurization. The upper surface of the water in buret 5 is set to the zero point again to measure the permanent increment (c) (state C).

The percentage of the permanent increment (c) the the total increment (d) is the permanent increment ratio which represents the pressure resistance of container 11.

After the completion of the measurement, container 11 is lifted from the principal water tank 1 and placed on the floor, the clamping plate 24 is retracted from neck 22 of second nozzle 16 to separate first nozzle 15 and second nozzle 16, and second nozzle 16 is then turned with operating handle 30 to release container 11, thus completing the procedure for a series of measurements.

Although vent 14 is provided in cover 8 in the embodiment as described hereinabove, vent 14 is not always necessarily provided in cover 8. A concave cover may be favorable for the smooth evacuation of air adhering to the inner surface of the cover. The series of operation can be automated by providing a switch 33 which generates a signal to acutate the power cylinder 25 upon the detection of complete insertion of joint 20 of second nozzle 16 into the joining part 18a of first nozzle 15 and switch 35 which gives a signal to actuate the high pressure air system (not shown) at the detection of the engagement of clamping plate 24 with neck 22 of second nozzle 16.

The structure of the present invention thus being constructed, the cover is placed on the upper brim of the principal water tank in the water contained in the auxiliary water tank after a container to be tested is immersed in the water contained in the principal water tank. Consequently, the air adhering to the inner surface of the cover is free to escape so that the deaeraring operation is eliminated. Furthermore, the time required for the operation of setting the zero point of the buret is reduced as a fixed quantity of the water in the principal water tank and the auxiliary water tank is restored during the replacement of the containers after a series of measurement operations reducing the time expended for resupplying water in the water tanks.

Still further, the junction of the first nozzle and the second nozzle is disposed outside of the principal water tank. The high pressure air leaked from the junction is released into the atmosphere without producing any effect on the measurement and the leakage of the high pressure air into the principal water tank is limited to only from the junction of the second nozzle and containers tested and reduced to a very small amount. Accordingly, accurate measurement of the total increment and the permanent increment is attained under regular conditions, thus providing accurate measurement and improving the efficiency of preparation of the measurement.

Obviously, many modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A water tank assembly for a pressure resistance measuring apparatus for testing containers comprising:
   a vertical water tank;
   an auxiliary water tank connected with said vertical water tank at an upper end portion of said vertical tank wherein said vertical tank has a smaller diameter than that of said auxiliary water tank;
   a cover attached to said vertical water tank;
   a nozzle assembly connected to said cover wherein a container to be tested is fixed to the lower end of the nozzle assembly, an opening end portion of said vertical water tank protruding into said auxiliary water tank, and wherein said vertical water tank and said auxiliary water tank store water and the water level of said auxiliary water tank is above said upper end portion of said vertical water tank.

2. A water tank assembly as set forth in claim 1, said cover having a through hole formed therein, wherein said nozzle assembly comprises a first and second nozzle member assembled to form a fluid passage, a bottom end portion of said first nozzle being fixed to an upper face portion of said cover, said second nozzle rotatably penetrating said cover from an interior portion to an exterior portion of said vertical water tank through said through hole formed in said cover, and said second nozzle having at its lower end a threaded portion for coupling said second nozzle with said container to be tested and at its upper end a joint connecting said second nozzle with said first nozzle.

* * * * *